United States Patent [19]
Sala et al.

[11] Patent Number: 5,480,882
[45] Date of Patent: Jan. 2, 1996

[54] BENZOXAZINONE AND BENZOTHIAZINONE DERIVATIVES HAVING CARDIOVASCULAR ACTIVITY

[75] Inventors: Alberto Sala, Monza; Roberto Barani, Paderno Dugnano; Francesca Benedini, Milan; Giorgio Bertolini, Sesto San Giovanni; Giancarlo Doná, Milan; Gianni Gromo, Milan; Silvio Levi, Milan, all of Italy

[73] Assignee: Italfarmaco S.p.A., Milan, Italy

[21] Appl. No.: 347,217

[22] Filed: Nov. 23, 1994

Related U.S. Application Data

[63] Continuation of Ser. No. 46,759, Apr. 15, 1993, abandoned.

[30] Foreign Application Priority Data

Apr. 16, 1992 [IT] Italy ................... MI92A0940

[51] Int. Cl.$^6$ ................ A61K 31/535; A61K 31/54; C07D 279/08; C07D 265/22
[52] U.S. Cl. .................. 514/224.2; 544/230.5; 544/50; 544/92
[58] Field of Search ............. 544/50, 92; 514/224.2, 514/230.5

[56] References Cited

U.S. PATENT DOCUMENTS

| | | | |
|---|---|---|---|
| 3,459,748 | 8/1969 | Krapcho | 260/243 |
| 3,539,563 | 11/1970 | Garzia | 260/244 |
| 5,071,850 | 12/1991 | Rieu | 514/229.8 |
| 5,189,034 | 2/1993 | Alberto et al. | 514/224.2 |

OTHER PUBLICATIONS

Burger, *Medicinal Chemistry*, 3rd ed. (1970), Part I pp. 74–75.
Noller, *Chemistry of Organic Compounds*, 2nd ed (1957) p. 272.

*Primary Examiner*—Philip I. Datlow
*Attorney, Agent, or Firm*—Oblon, Spivak, McClelland, Maier & Neustadt

[57] ABSTRACT

Compounds of formula I

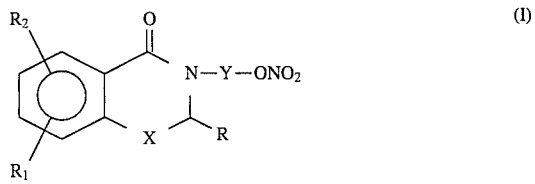

wherein

R represents hydrogen, $C_1$–$C_6$ alkyl, $C_5$–$C_7$ cycloalkyl, methylene-dioxy or phenyl, which may be substituted by one or two groups independently selected from hydroxy, halogen, nitro, $C_1$–$C_6$ alkyl or $C_1$–$C_6$ alkoxy; $R_1$ and $R_2$ independently represent hydrogen, $COOR_3$, —$CONR_4R_5$,

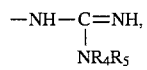

—$OCONR_4R_5$, —$OCOR_3$, —$NR_4R_5$, —$OCOOR_6$, —$NR_3COR_7$, —$NR_{CONR4}R_5$, —$N=CH$—$NR_4R_5$, $NO_2$, CN, OH, $SR_3$, wherein $R_3$ is hydrogen or $C_1$–$C_6$ alkyl, $R_4$ and $R_5$ independently are hydrogen or $C_1$–$C_6$ alkyl, $R_6$ is $C_1$–$C_6$ alkyl, and $R_7$ is hydrogen, $C_1$–$C_6$ alkyl or $C_1$–$C_6$ alkoxy, with the proviso that $R_1$ and $R_2$ cannot be hydrogen at the same time; X is oxygen or sulphur; Y represents a $C_2$–$C_6$ alkylene chain or a $C_5$–$C_7$ cycloalkylene group; and their pharmaceutically acceptable salts are provided, and their use in pharmaceutical compositions which may be used in the treatment of cardiovascular diseases.

9 Claims, No Drawings

BENZOXAZINONE AND BENZOTHIAZINONE DERIVATIVES HAVING CARDIOVASCULAR ACTIVITY

This application is a Continuation of application Ser. No. 08/046,759, filed on Apr. 15, 1993, now abandoned.

BACKGROUND OF THE INVENTION

1. Field of the Invention

The present invention relates to nitrooxy-containing compounds of formula I

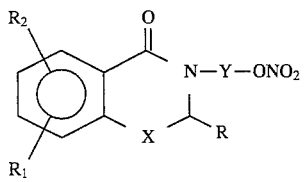

(I)

and their pharmaceutically acceptable salts, pharmaceutical compositions containing them, and a method for treating cardiovascular diseases utilizing these compounds and compositions.

2. Discussion of the Background

N-unsubstituted 2,3-dihydro-4H-1,3-benzoxazin-4-ones are described by B. W. Horrom et al., *J. Org. Chem.*, 72, 721, 1950, which discloses 2,3-dihydro-2-phenyl-4H-1,3-benzoxazin- 4-one as having analgesic activity. Other 2,3-dihydro- 4H-1,3-benzoxazin-4-ones are described by R. B. Gammill, *J. Org. Chem.*, 46, 3340, 1981.

N-substituted derivatives of the same heterocycle were disclosed by J. Finkelstein et al., *J. Med. Chem.*, 11 1038, 1968, and they seem to possess anti-inflammatory activity. Finally analogous derivatives bearing an amine group in 6-position and having anti-inflammatory activity were disclosed by F. Fontanini et al., *Riv. Farmacol. Ter.*, 4(1), 119, 1973 (Chem. Abs. 73745n, Vol. 79, Page 40, 1973).

The medical field has long desired to have a compound effective in treating cardiovascular diseases, which minimizes undesirable side-effects, while maintaining potency and effectiveness.

SUMMARY OF THE INVENTION

Accordingly, one object of the present invention is to provide benzoxazinone and benzothiazinone derivatives of formula I which contain nitrooxy substituents and their pharmaceutically acceptable salts, which are effective cardiovascular agents.

Another object of the present invention is to provide pharmaceutical compositions, containing as active ingredient, the nitrooxy-containing compounds of formula I, useful in treatment of cardiovascular diseases.

Another object of the present invention is to provide a method for treatment of cardiovascular diseases utilizing the compounds of formula I.

These and other objects of the present invention have been satisfied by the discovery of nitrooxy-containing compounds of formula I

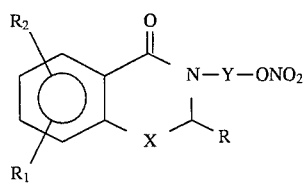

(I)

wherein
R represents hydrogen, $C_1$–$C_6$ alkyl, $C_5$–$C_7$ cycloalkyl, phenyl, which may be substituted by one or two groups independently selected from hydroxyl, halogen, nitro, $C_1$–$C_6$ alkyl or $C_1$–$C_6$ alkoxy, or methylene-dioxy; $R_1$ and $R_2$ independently represent hydrogen, —$COOR_3$, —$CONR_4R_5$,

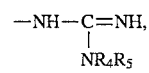

—$OCONR_4R_5$, —$OCOR_3$, —$NR_4R_5$, —$OCOOR_6$, —$NR_3COR_7$, —$NR_3CONR_4R_5$, —N=CH—$NR_4R_5$, $NO_2$, CN, OH, $SR_3$, wherein $R_3$ is hydrogen or $C_1$–$C_6$ alkyl, $R_4$ and $R_5$ independently are hydrogen or $C_1$–$C_6$ alkyl, $R_6$ is $C_1$–$C_6$ alkyl, and $R_7$ is hydrogen, $C_1$–$C_6$ alkyl or $C_1$–$C_6$ alkoxy, with the proviso that $R_1$ and $R_2$ cannot be hydrogen at the same time; X is oxygen or sulphur; Y represents a $C_2$–$C_6$ alkylene chain or a $C_5$–$C_7$ cycloalkylene group; and the pharmaceutically acceptable acid or basic salts thereof, which are useful in a method for treating cardiovascular disease.

DETAILED DESCRIPTION OF THE PREFERRED EMBODIMENTS

The present invention relates to 2,3-dihydro-4H-1,3-benzoxazin- 4-ones and 2,3-dihydro-4H-1,3-benzothiazin-4-ones of formula I

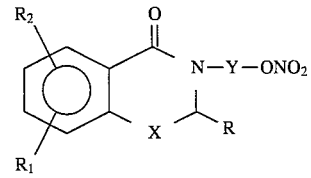

(I)

wherein
R represents hydrogen, $C_{1-6}$ alkyl, $C_5$–$C_7$ cycloalkyl, phenyl, which may be substituted by one or two groups independently selected from hydroxy, halogen, nitro, $C_1$–$C_6$ alkyl or $C_1$–$C_6$ alkoxy, or methylene-dioxy; $R_1$ and $R_2$ independently represent hydrogen —$COOR_3$, —$CONR_4R_5$,

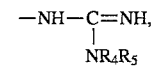

—$OCONR_4R_5$,—$OCOR_3$, —$NR_4R_5$, —$OCOOR_6$, —$NR_3COR_7$, —$NR_3CONR_4R_5$, — N=CH—$NR_4R_5$, $NO_2$, CN, OH, $SR_3$, wherein $R_3$ is hydrogen or $C_1$–$C_6$ alkyl, $R_4$ and $R_5$ independently are hydrogen or $C_1$–$C_6$ alkyl, $R_6$ is $C_1$–$C_6$ alkyl, and $R_7$ is hydrogen, $C_1$–$C_6$ alkyl or $C_1$–$C_6$ alkoxy, with the proviso that $R_1$ and $R_2$ cannot be hydrogen at the same time; X is oxygen or sulphur; Y represents a $C_2$–$C_6$ alkylene chain or a $C_5$–$C_7$ cycloalkylene group; and the pharmaceutically acceptable acid or basic salts thereof.

The $C_1$–$C_6$ alkyl group may be linear or branched. Examples of the $C_1$–$C_6$ alkyl group include methyl, ethyl, propyl, isopropyl, butyl, 2-methylpropyl, n-pentyl, 3-methylbutyl, isopentyl, and n-hexyl.

The $C_1$–$C_6$ alkoxy group may also be linear or branched. Examples of the $C_1$–$C_6$ alkoxy group include methoxy, ethoxy, propoxy, isopropoxy, butoxy, 2-methylbutoxy and tert.butoxy.

The $C_2$–$C_6$ alkylene chain of the present invention may likewise be a linear or branched alkylene chain. Examples of the $C_2$–$C_6$ alkylene chain include ethylene, 2-methylethylene, 1,3-propylene, 1,4-butylene, 2-ethylethylene, 2-methylpropylene, 1,5-pentylene, 2-ethylpropylene, 2-methylbutylene, 1,6-hexylene, 1-ethyl-1-methylpropylene, and 3-methylpentylene.

The $C_5$–$C_7$ cycloalkylene group is a divalent cycloalkyl group having from 5 to 7 carbons in the substituent. Examples of the $C_5$–$C_7$ cycloalkylene group include 1,2-cyclopentylene, 1,3-cyclopentylene, 1,2-cyclohexylene, 1,3-cyclohexylene, 1,4-cyclohexylene, 1,2-cycloheptylene, 1,3-cycloheptylene and 1,4-cycloheptylene, wherein the numbers preceding the ring name designate the sites of connection of the ring to the remainder of the molecule of the compounds of the present invention.

The compounds of the invention may be prepared according to a process comprising, as the first step, the formation of a 2,3-dihydro-1,3-benzoxazine or 2,3-dihydro-1,3-benzothiazine derivative of formula IV

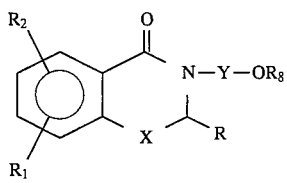

(IV)

wherein R, $R_1$, $R_2$, X and Y have the above meanings, and is hydrogen or a $C_2$–$C_4$ acyl group, by condensing a salicylamide of formula II

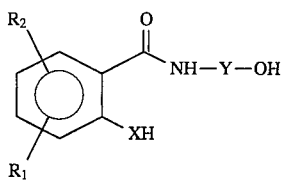

(II)

wherein $R_1$, $R_2$, X and Y are as defined above, with an aldehyde of formula III R—CHO  III wherein R has the above meanings, or a derivative or precursor thereof.

The $C_2$–$C_4$ acyl group of $R_8$ in formula IV may be any carbonyl-based acyl group. Examples of the acyl group include acetyl, propionyl, butyroyl, and isobutyroyl.

The condensation of II with III can be performed in acid medium, such as in a strong mineral acid combined with acetic acid, whereby compounds of formula IV (wherein $R_8$ is acetyl) are obtained. Alternatively, the condensation may be performed by using molecular sieves in the presence of a sulphonic acid, such as p-toluensulphonic acid, methanesulphonic acid, α- and β-naphthalenesulphonic acids, or phosphoric acid, or esters and analogues thereof.

The condensation is carried out in the presence of an organic solvent. Suitable solvents include inert organic solvents, such as ethyl acetate, acetonitrile, benzene, toluene, nitrobenzene or chlorobenzene; halogenated aliphatic hydrocarbons such as methylene chloride, chloroform, 1,2-dichloroethane or 1,1,2-trichloroethylene; cyclohexane, tetrahydrofuran, tetrahydropyran, dimethylformamide, or dimethylacetamide. The reaction temperature may vary widely without adversely affecting the reaction, with the preferred range of temperature being between about $-10°$ C. and the reflux temperature of the reaction mixture. The reaction time is a time period varying from about 2 to about 30 hours, preferably 2 to 15 hours.

The relative molar amounts of reactants of formula II and III are not critical for the cyclization to proceed, since the reaction itself is self balancing in stoichiometry. In other words, only one molecule of II reacts with one molecule of III. Therefore, any excess of either component is inconsequential. This allows for use of the components II and III in a wide range of stoichiometric ratios, with ratios close to 1:1 preferred to avoid waste of one of the reactants.

When 2,3-dihydro-4H-1,3-benzoxazinones or -benzothiazinones are desired wherein R is hydrogen or methyl, a precursor of the compound of formula III, such as paraformaldehyde or acetaldehyde trimer is preferably employed. This precursor then acts as formaldehyde and acetaldehyde under the conditions of the reaction.

The 2,3-dihydro-1,3-benzoxazine or -benzothiazine derivatives of formula IV wherein $R_8$ is $C_2$–$C_4$ acyl can then be transformed into the desired compounds of formula I as shown in the following reaction scheme.

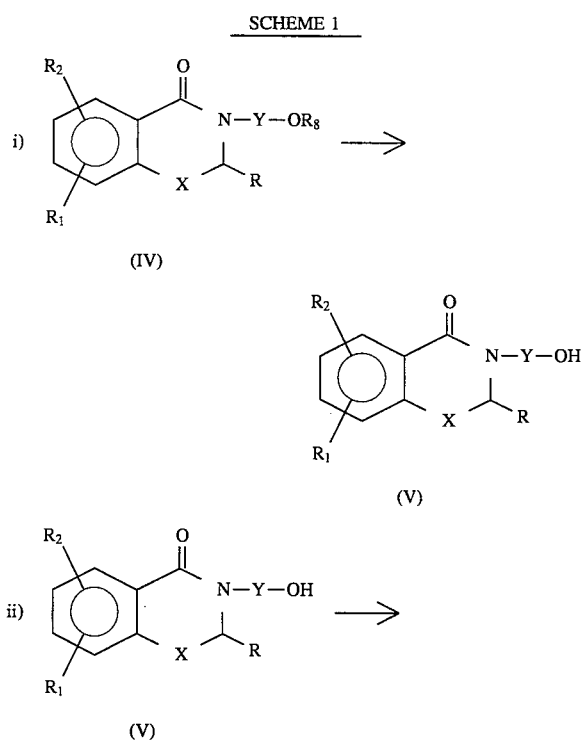

SCHEME 1

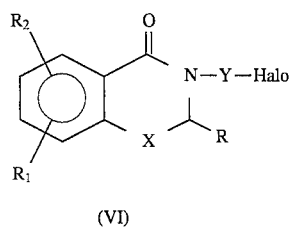

(VI)

wherein R, $R_1$, $R_2$, $R_8$, X and Y are as defined above, and Halo is halogen. According to step i) of Scheme 1, the compound of formula IV is transformed into compound V through hydrolysis in an alkaline aqueous, alcoholic or aqueous/alcoholic medium, for example, by treatment with an alkali or earth-alkaline metal carbonate or hydrocarbonate in methanol or ethanol, at room temperature for about 10–15 hours.

The free OH group of V is then replaced with a halogen atom by means of conventional halogenating agents, such as, thionyl chloride, sulphuryl chloride, phosphorous trichloride, phosphorous pentachloride, phosphorous oxytrichloride, phosphorous tribromide and sulphuryl bromide. The reaction proceeds in an organic solvent, preferably in an inert organic solvent as described above for the preparation of the heterocycle of formula IV, at a temperature varying between about 25° C. and the reflux temperature of the reaction mixture. One of ordinary skill in organic synthesis would readily recognize that when the condensation of compounds of formula II and III yields a compound of formula IV wherein $R_8$ is hydrogen, step i) is omitted and the compound of formula IV, wherein $R_8$ is hydrogen is submitted directly to step ii) of Scheme 1.

The compounds of formula VI are then converted into the desired products of formula I through procedures for converting the halo substituent into the —$ONO_2$ group. One suitable procedure is by treatment of VI with silver nitrate in the presence of an organic solvent such as acetonitrile. Preferably, a molar excess of silver nitrate with respect to the compound of formula VI is employed, and the reaction is carried out at a temperature between the boiling temperature of the reaction mixture and about 25° C. The reaction is completed in a time period of from about 2–6 hours. The desired final products of formula I can then be isolated and purified using conventional techniques.

A preferred embodiment relates to compounds of formula I substituted by nitro in the 6-position, which can be obtained starting from a compound of formula VII

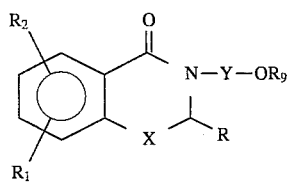

(VII)

wherein R, X and Y are as defined above, $R_1$ and $R_2$ are each hydrogen and $R_9$ represents hydrogen or a nitro group. Compound VII is reacted with fuming nitric acid at a temperature ranging from about −20° C. to about 0° C. for a time period varying between about 10 minutes and about 2 hours, to provide a compound of formula I

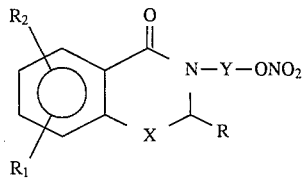

(I)

wherein R, X and Y are as defined above, $R_1$ is hydrogen, and $R_2$ represents a nitro group in the 6-position.

This 6-nitro compound may be catalytically hydrogenated at a temperature of 10°–40° C., in an alcohol solvent, for from about 30 minutes to 5 hours, using a conventional hydrogenation a common catalyst such as palladium or platinum sponge, to provide a compound of formula V

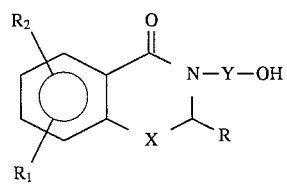

(V)

wherein R, X and Y are as defined above, $R_1$ is hydrogen, and $R_2$ is a primary amine group in the 6-position. Compound V can be transformed to the corresponding 6-amino compound of formula I by transforming the OH group to a —$ONO_2$ as shown in steps ii) of Scheme 1.

Alternatively, the compound of formula V may be converted into another compound of formula I by means of suitable procedures of modification of the 6-amino residue using conventional organic synthetic methods.

For example, one can transform the 6-amino group into an —$NR_3COR_7$ group, wherein $R_3$ and $R_7$ are as defined above, by reacting compounds of formula V with a suitable acyl halide $R_7$—CO-Halo, wherein Halo is a halogen atom, or an anhydride $(R_7CO)_2O$.

The transformation of the 6-amino group of compound V into an —$NR_3$—CO—$NR_4R_5$ group, wherein $R_4$ and $R_5$ are as defined above, may be conducted using a suitable carbamoyl halide of formula $R_4R_5N$—CO-Halo, wherein Halo is a halogen atom. The preparation of compounds of V where R, X and Y are as defined above, $R_1$ is hydrogen and $R_2$ is —N=CH—$NR_4R_5$, may be effected by reacting the 6-amino group with a formamide of formula CHO—$NR_4R_5$, wherein $R_4$ and $R_5$ are as defined above, in the presence of thionyl chloride.

The transformation of the 6-amino group to OH, $NO_2$, CN or $SR_3$, wherein $R_3$ is as defined above, may be effected by diazotizing compound V using conventional methods, such as treatment with an alkali nitrate in the presence of a mineral acid such as hydrochloric, nitric, or sulphuric acid. The diazonium salt thus formed is submitted to a substitution reaction in the presence of a copper(I) salt, and the diazonium group is replaced by a group selected from the group consisting of OH, $NO_2$, CN, $SR_3$, wherein $R_3$ is as defined above, to provide a compound of formula V

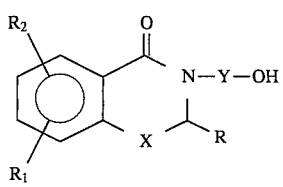

(V)

wherein R, X and Y are as defined above, $R_1$ is hydrogen and $R_2$ is OH, $NO_2$, CN or $SR_3$ in the 6-position.

Upon preparation of the desired compound of formula V having the desired 6-position substituent, as described above, the compound of formula V may be readily converted to a compound of formula I by the nitration procedures, such as previously depicted in Scheme 1.

The interconversion of $R_1$ or $R_2$ into another of the groups defined for $R_1$ or $R_2$ may be performed according to conventional procedures known to those of ordinary skill in the art. These procedures fall within the scope of the present invention, as well as the obvious modification of the preparation methods of the compounds of the invention described above.

The starting amides of formula II are known substances or may be prepared through conventional methods from the corresponding salicylates or thiosalicylates of formula VIII

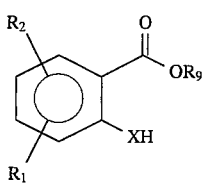

(VIII)

wherein $R_1$, $R_2$ and X have the above meanings, and $R_9$ is a $(C_1-C_4)$-alkyl, preferably methyl. In turn, the compounds of formula VIII are known from the literature or are synthesized according to conventional procedures starting from the corresponding salicylic and thiosalicylic acids.

The aldehydes of formula III, the derivatives and precursors thereof, are commercial products, or can be prepared according to conventional methods. The compound of formula VII may be prepared through one or more of the reactions described in the above Scheme 1.

The compounds of the present invention exhibit cardiovascular activity. In particular, they showed noticeable vasodilative properties in vitro, and a remarkable antianginal activity in laboratory animals.

These favorable biological properties are accompanied by a negligible hypotensive effect, which is one of the undesired side-effects of the known nitroderivatives used in therapy.

Thus, the compounds of the invention may be considered as potential drugs with specific anti-anginal activity. Additionally, they possess anti-arrhythmic activity. This antiarrhythmic activity is especially desired since angina attacks are often accompanied by arrhythmias of varying intensity.

The vasodilative activity of the compounds of the present invention were determined by testing of a rabbit aorta strip contracted with noradrenaline. Using the method described by K. Murakami et al. *Eur. J. Pharmacol.*, 141, 195, 1987., $IC_{50}$ values (i.e. the micromolar (µM) concentrations of active substances causing a 50% inhibition of the contraction of the aorta strip), were determined.

The results obtained with representative compounds of the present invention are set forth in the following Table 1.

TABLE 1

| Compound of Example | Vasodilative activity in vitro $IC_{50}$ (µM) |
|---|---|
| 1 | 0.021 |
| 2 | 0.27 |
| 3 | 0.64 |
| 4 | 0.071 |
| 5 | 0.096 |
| 6 | 0.057 |

The in vivo antianginal activity was determined on anaesthetized Sprague Dawley rats of weight 350–400 g, in accordance with the method of M. Leitold et al., *Arzeim. Forsch.*, 36, 1454 1986. The test was carried out by intravenously administering to the animals one I.U./Kg, equivalent to 3 mg/Kg of Arg-vasopressin, thus inducing a reproducible coronary spasm that may be electrocardiographically monitored by an increase of the T-wave. The animals were treated intravenously with 4 increasing doses of the compounds of the present invention to measure their $ED_{50}$ (i.e., the dose giving 50% inhibition of the T-wave increase).

The results obtained for representative compounds of the present invention are set forth in Table 2.

TABLE 2

| Compound of Example | Antianginal activity in vivo $ED_{50}$ (µg/Kg) |
|---|---|
| 1 | 63.7 |
| 2 | 21.0 |
| 3 | 9.7 |
| 4 | 11.5 |

In another embodiment of the present invention the compounds of the present invention can be incorporated into pharmaceutical compositions for use in treating various cardiovascular diseases which require administration of vasodilating or anti-anginal agents. These pharmaceutical compositions may take any form suitable for administration to a subject requiring treatment. Suitable pharmaceutical compositions include uncoated tablets, coated tablets which may be coated with such things as sugar or biologically acceptable films, syrups and vials, the latter being suitable both for oral, intramuscular or intravenous administration. These compositions contain the active substance alone or in combination with the usual pharmaceutically acceptable carriers and excipients.

The dosages of active substance employed to combat, for example, an anginal attack may vary within wide limits according to the kind of compound used and they are chosen to ensure the most effective therapeutic coverage throughout a 24 hour cycle. Preferred dosages are from 1 to 200 g/Kg, preferably from 10 to 100 µg/Kg.

Having generally described this invention, a further understanding can be obtained by reference to certain specific examples which are provided herein for purposes of illustration only and are not intended to be limiting unless otherwise specified.

The $^1$H-NMR spectra reported below were recorded in dimethylsulphoxide (DMSO) with a VARIAN GEMINI 200 spectrometer. The $^{13}$C-NMR spectra were recorded by using a VARIAN GEMINI 200 spectrometer, taking the dimethylsulphoxide (DMSO) 39.5 ppm peak as the reference peak.

EXAMPLE 1

2,3-Dihydro-3-(2'-nitrooxyethyl)-6-nitro,4H-1,3-benzoxazin-4-one

A) A solution of 18.5 g (0.102 mole) of N-(2'-hydroxyethyl) salicylamide prepared as described in *Aust. J. Chem.*, 25, 1797 1972, in 500 ml of chloroform and 11 ml of glacial acetic acid was combined with 5.5 g of paraformaldehyde. The mixture was cooled to 0° C. and 10 g of gaseous hydrochloric acid was added over a period of 30 minutes, and the resulting solution stirred at room temperature for 24 hours. The oily layer was discarded and the chloroform layer was washed with water and dried over sodium sulphate. The crude residue obtained, after evaporation of the solvent, was purified by silica gel column chromatography by eluting with methylene chloride/acetone (85/15 v/v). 13 g of 3-(2'-acetoxyethyl)-2,3-dihydro-4H-1,3-benzoxazin-4-one were recovered. m.p. 49°–51° C. (acetone).

B) A solution of 13 g (0.055 mole) of the compound prepared under A), in 230 ml of methanol was combined with 2.75 g (0.026 mole) of sodium carbonate, and the resulting mixture left at room temperature for 12 hours. The crude residue obtained after evaporation of the solvent, was taken up with methylene chloride, and the resulting organic layer washed with water and dried over sodium sulphate. After evaporation of the solvent, 9.5 g of 2,3-dihydro-3-(2'-hydroxyethyl)-4H-1,3-benzoxazin-4-one were obtained. m.p. 59°–61° C. (methylene chloride/acetone 1/9 v/v).

C) The product obtained under B) (9 g, 0.046 mole) dissolved in 70 ml of chloroform, and 3.54 ml (0.048 mole) of thionyl chloride was added dropwise to the resulting solution. The solution was then heated at 70° C. for 3 hours. After washing with 5% sodium bicarbonate and water, drying over sodium sulphate, and subsequent evaporation of the solvent, 9.3 g of 3-(2'-chloroethyl)-2,3-dihydro-4H-1,3-benzoxazin-4-one were obtained. m.p. 45°–47° C. (n-hexane).

D) The product obtained under C) (5.0 g, 0.023 mole) was dissolved in 50 ml of acetonitrile, and 6 g (0.035 mole) of silver nitrate in 35 ml of acetonitrile were added to the resulting solution. The reaction mixture was heated at 85° C. for 2 hours and then cooled to room temperature. The salts formed during reaction were removed by filtration, and the solvent was removed by evaporation. The resulting crude product was taken up with methylene chloride and the organic layer washed with water and dried over sodium sulphate. After evaporation of methylene chloride, 4.8 g of 2,3-dihydro-3-(2'-nitrooxyethyl)-4H-1,3-benzoxazin-4-one were obtained. m.p. 49°–51° C. (n-hexane).

E) 50 ml of 100% fuming nitric acid were dropped into 50 g (0.21 mole) of 2,3-dihydro-3-(2'-nitrooxyethyl)-4H-1,3-benzoxazin-4-one, at a temperature of −10° C. At the end of the addition, the reaction mixture was stirred for minutes, then poured in ice and sequentially extracted with chloroform. The organic layer was washed with water, sodium hydroxide 0.1N and again with water, then dried over sodium sulphate and concentrated to dryness. The resulting oil was taken up with warm ethyl ether yielding 42.5 g of the title compound as white solid. m.p. 97°–99° C. (ethyl ether).

$^1$H-NMR 8.54 (d, 1H); 8.40 (dd, 1H); 7.58 (d, 1H); 5.55 (s, 2H); 4.74 (t, 2H); 3.90 (t, 2H)

$^{13}$C-NMR 162.39; 160.48; 142.64; 129.69; 123.70; 118.83; 118.57; 78.89; 71.54; 41.73

EXAMPLE 2

6-Acetamido-2,3-dihydro-3-(2'-nitrooxyethyl)-4H-1,3-benzoxazin-4-one

A) A solution of 42 g (0.148 mole) of the compound of Example 1 in 6,300 ml of methanol was combined with 10% Pd/C, and the resulting mixture was placed in a hydrogen atmosphere having a head of water, at room temperature. At the end of the reaction, the suspension was filtered on celite and the solution obtained was evaporated under vacuum. The resulting crude product was taken up with ethyl ether and filtered under vacuum, thus yielding 30 g of 6-amino-2,3-dihydro-3-(2'-hydroxyethyl)-4H-1,3-benzoxazin-4-one. m.p. 94°–96° C. (ethyl ether).

B) 200 ml of chloroform at 0° C. were combined with 13 g (0.057 mole) of the compound prepared under A and 6.3 g (0.063 mole) of triethylamine. Into the resulting suspension, 10 g (0.014 mole) of acetyl chloride were dropped. The resulting solution was stirred for 1 hour at 0° C., and then for 18 hours at room temperature. Finally the solution was washed with water, 5% sodium bicarbonate, and again with water, then concentrated to dryness. The resulting solid was treated with sodium hydroxide 1N, concentrated to small volume and taken up with chloroform. The organic layer was separated, washed with water, dried and evaporated to dryness. Crystallization of the resulting product yielded 7.2 g of 6-acetamido-2,3-dihydro-3-(2'-hydroxyethyl)-4H-1,3-benzoxazin-4-one. m.p. 155°–156° C. (acetone).

C) A solution of 2.75 ml (0.037 mole) of thionyl chloride in 7 ml of chloroform was added dropwise to a solution of 7.0 g (0.028 mole) of the compound prepared under B, in 49 ml of chloroform. At the end of the addition, the reaction was heated at reflux for 1 hour. After cooling, the resulting solution was washed twice with 5% sodium bicarbonate, and once with water, and dried over sodium sulphate. After evaporation of chloroform, the resulting oil was taken up with 10 ml of ethyl ether, and added dropwise to 60 ml of n-hexane at 0° C., and the resulting precipitate was filtered under vacuum and dried to yield 6.3 g of 6-acetamido-3-(2'-chloro- ethyl)-2,3-dihydro- 4H-1,3- benzoxazin-4-one. m.p. 133°–135° C. (ethyl ether/n-hexane).

D) A solution of 7.26 g (0.042 mole) of silver nitrate in 30 ml of acetonitrile was added dropwise to a solution of 6.0 g (0.023 mole) of the compound obtained under C) in 45 ml of acetonitrile. At the end of the addition, the reaction mixture was left at reflux for 3 hours and then cooled to 0° C. The salts formed during reaction were removed by filtration and the solvent was removed by evaporation. The resulting crude product was taken up with chloroform, filtered and concentrated to dryness under vacuum yielding 2,3 g of the title product. m.p. 141°–142° C. (acetone).

$^1$H-NMR 10.03 (s, 1H); 8.07 (d, 1H); 7.70 (dd, 1H); 7.03 (d, 1H); 5.33 (s, 2H); 4.71 (t, 2H); 4.28 (t, 2H); 2.05 (s, 2H)

$^{13}$C-NMR 168.41; 161.90; 153.44; 134.50; 125.53; 118.55; 117.99; 116.88; 78.42; 71.72; 41.49; 24.11

EXAMPLE 3

2,3-Dihydro-6-(N',N',-dimethyl-N-formimido)-3-(2'-nitro-oxyethyl)-4H-1,3-benzoxazin-4-one-HCl A) A solution of 200 ml of thionyl chloride and 5 ml of dimethylformamide, at 0° C., was combined with 10 g (0.048 mole) of the compound obtained in Example 2A, in portions. The resulting solution was poured in ice and neutralized by repeated dropwise addition of sodium hydroxide, while maintaining the temperature at about 0° C. The aqueous solution was extracted with chloroform and dried over sodium sulphate. The solvent was evaporated and the resulting solid was taken up with ethyl ether, filtered and dried yielding 9.2 g of 2,3-dihydro6-(N'N'-dimethyl-N-formimido)-3-(2'-chloroethyl)-4H-1,3-benzoxazin-4-one. m.p. 94°–95° C. (ethyl ether).

B) By employing 9 g (0.032 mole) of the compound prepared under A, the same reaction of the Example 2D was carried out. The resulting oil was taken up with hydrochloric ether, and the formed precipitate was filtered and dried under vacuum yielding 4.5 g of the title product. m.p. 140° C. (ethyl ether).

$^1$H-NMR 12.03 (s, 1H); 8.79 (s, 1H); 7.99 (d, 1H); 7.84 (dd, 1H); 7.19 (d, 1H); 5.41 (s, 2H); 4.74 (t, 2H); 3.89 (t, 2H); 3.37 (s, 6H)

$^{13}$C-NMR 161.40; 155.62; 153.95; 133.07; 126.07; 119.17; 118.44; 117.86; 78.48; 71.67; 43.59: 41.59; 38.27

EXAMPLE 4

6-Ciano-2,3-dihydro-3-(2'-nitrooxyethyl)-4H-1.3-benzoxazin- 4-one

A) A solution of 9.7 g (0.547 mole) of 5-cyanosalicylic acid methyl ester (prepared as described in *Chem. Pharm. Bull.*, 1984, 38, 4466–4477) in 15 ml of acetonitrile, was combined with 4.01 g (0.65 mole) of ethanolamine, and then heated at reflux for 24 hours. At the end of the 4th and 7th hours, two further portions of 1 g (0.016 mole) each of ethanolamine were added. At the end of the heating, the solution was evaporated to dryness under vacuum, taken up with ethyl acetate and washed with hydrochloric acid 1N and then with water. The organic layer was dried over sodium sulphate and concentrated to small volume. The formed solid was filtered and dried under vacuum yielding 9.2 g of 5-cyano-(2-hydroxyethyl)salicylamide. m.p. 144°–146° C. (acetonitrile).

B) A mixture of 8 g (0.0388 mole) of the compound prepared under A, 2.79 g (0.0931 mole) of paraformaldehyde and 2.95 g (0.0155 mole) of p-toluensulphonic acid in 200 ml of acetonitrile was heated to reflux for 1 hour. After evaporation of the solvent, the residue was taken up in water, filtered and dissolved in 20 ml of trifluoroacetic acid. After stirring at room temperature for 18 hours, 100 ml of water were added and the precipitated solid was filtered and washed thoroughly with water. The resulting product was suspended in 100 ml of methanol and 10 ml of sodium hydroxide, and stirred at room temperature until completely dissolved. After addition of 300 ml of chloroform, the organic layer was separated, washed with water, dried and evaporated. The residue was dissolved in acetone and precipitated with n-hexane yielding 2.45 g of 6-ciano-2,3-dihydro-3-(2'-hydroxyethyl)-4H-1,3-benzoxazin-4-one. m.p. 102°–103° C. (acetone/n-hexane).

C) 2.08 g (0.00953 mole) of the compound prepared under B were dissolved in 40 ml of chloroform stabilized with amylene, and 0.78 ml (0.0107 mole) of thionyl chloride was added dropwise to the resulting solution. The reaction mixture was then heated at 70° C. for 2 hours. After cooling, the solution was washed with 5% sodium bicarbonate and water, and dried over sodium sulphate. After evaporation of the solvent, 1.85 g of 6-ciano-3-(2'-chloroethyl)-2,3-dihydro-4H-1,3-benzoxazin-4-one were obtained. m.p. 118°–120° C. (ethyl ether).

D) A solution of 5.68 g (0.033 mole) of silver nitrate in 10 ml of acetonitrile was added to a solution of 1.76 g (0.00745 mole) of the compound obtained under C) in 50 ml of acetonitrile. At the end of the addition, the reaction mixture was heated to 85° C. for 4 hours, and then cooled to room temperature. The salts formed during reaction were removed by filtration and the solvent removed by evaporation. The resulting crude product was taken up with ethyl acetate, and the organic layer was washed with water and dried over sodium sulphate. After evaporation of the solvent 1.0 g of the title product was obtained. m.p. 132°–134° C. (ethyl acetate).

$^1$H-NMR 8.21 (d, 1H); 8.01 (dd, 1H); 7.30 (d, 1H); 5.50 (s, 2H); 4.73 (t, 2H); 3.88 (t, 2H)

$^{13}$C-NMR 160.96; 160.41; 138.13; 132.72; 119.45; 118.59; 118.32; 105.52; 78.68; 71.57; 41.67

EXAMPLE 5

2,3-Dihydro-6-hydroxy-3-(2'-nitrooxyethyl)-4H-1,3-benzoxazin- 4-one

A) A solution of 50 g (0.32 mole) of 2,5-dihydroxybenzoic acid in 260 ml of methanol, at 0° C., was combined with 33 ml of sulphuric acid. The resulting solution was heated to 70° C. under stirring. After 6 hours the reaction mixture was cooled to room temperature and concentrated to small volume under vacuum. The resulting oily layer was taken up with sodium hydroxyde 5N and extracted with ethyl acetate the organic layer was washed with water, dried over sodium sulphate and evaporated under vacuum, to provide 52 g of methyl 2,5-dihydroxybenzoate which were used in the next step as obtained.

B) A mixture of 52 g (0.31 mole) of the compound obtained under A) and 22.4 ml (0.37 mole) of ethanolamine was heated to 170° C. while distilling off the resulting methanol. After 3 hours the solution was cooled to room temperature and taken up with a saturated solution of sodium chloride, acidified with HCl 1N to pH=2 and extracted with ethyl acetate. The organic layer was dried over sodium sulphate and evaporated under vacuum. Crystallization of the crude product with ethyl acetate/n-hexane yielded 51 g of N-(21-hydroxymethyl)-2,5-dihydroxy-benzamide. m.p. 142°–144° C. (ethyl acetate/n-hexane 9:1).

C) A suspension of 49 g (0.25 mole) of the compound obtained under B), in 500 ml of ethyl acetate, was combined with 15 g (0.5 mole) of paraformaldehyde and 4.7 g (0.02 mole) of p-toluene-sulphonic acid. The resulting mixture was heated to relux for 1 hour, then cooled to room temperature and washed with water. The separated organic layer was dried and evaporated under vacuum, giving 65.5 g of crude product which were taken up with 1.3 .L of a 1:1 solution of HCl 1N/tetrahydrofurane, and heated to 40° C. for 3 hours. The mixture was cooled to room temperature, saturated with sodium chloride and extracted with ethyl acetate. The organic layer was dried over sodium sulphate and evaporated under vacuum, to give 48 g of crude product. Purification by silica gel chromatography (eluent: ethyl acetate) provided 2.9 g of 2,3-dihydro-6-hydroxy-3-(2'hydroxyethyl)-4H-1,3-benzoxazin-4-one. m.p. 148°–150° C. (ethyl acetate).

D) From 20 g (0.096 mole) of the compound obtained under C and following the procedure used in Example 1C, 21 g of 3-(2'-chloroethyl)-2,3-dihydro-6-hydroxy-4H-1,3-benzoxazin- 4-one were obtained and used as such in the subsequent step.

E) From 10 g (0.05 mole) of the compound obtained under D and following the procedure used in Example 1D, 3.4 g of the title compound were obtained. m.p. 80°–82 C. ( ethyl acetate/n-hexane 1:1).

$^1$H-NMR 9.49 (s, 1H); 7.17 (d, 1H); 6.94 (m, 2H); 5.27 (s, 2H); 4.70 (t, 2H); 3.83 (t, 2H)

$^{13}$C-NMR 162.03; 152.74; 150.72; 121.92; 119.15; 117.57; 112.74; 78.39; 71.72; 41.43

EXAMPLE 6

2,3-Dihydro-7-hydroxy-3-(2'-nitrooxyethyl)-4H-1,3-benzoxazin- 4-one

A) From 20 g (0.1 mole) of N-(2'-hydroxyethyl)-2,4-dihydroxy-benzamide, and following the procedure used in Example 5D, 3 g of 2,3-dihydro-7-hydroxy-3-(2'-hydroxyethyl)- 4H-1,3-benzoxazin-4-one were obtained. m.p. 182°–184° C. (ethyl acetate/n-hexane 9:1).

B) From 2.5 g (0.01 mole) of the compound obtained in A), and following the procedure used in Example 1C, 1,7 g of 3-(2'-chloroethyl)-2,3-dihydro-7-hydroxy-4H-1,3-benzoxazin- 4-one were obtained, and used in the next step as such.

C) From 1.7 g (0.007 mole) of the compound obtained under B), and following the procedure used in Example 1D, 850 mg of the title compound were obtained. m.p. 131°–133° C. (ethyl acetate/n-hexane 1:1).

$^1$H-NMR 10.42 (s, 1H); 7.64 (d, 1H); 6.58 (dd, 1H); 6.38 (d, 1H); 5.30 (s, 2H); 4.69 (t, 2H); 3.81 (t, 2H)

$^{13}$C-NMR 163.13; 162.23; 159.70; 129.79; 111.02; 102.24; 78.49; 71.87; 41.21

EXAMPLE 7

2,3-Dihydro-7-isobutyroyloxy-3-(2'-nitrooxyethyl)-4H-1,3-benzoxazin-4-one

A) A solution of 1 g (0.0044 mole) of the compound obtained in Example 6B, in 10 ml of tetrahydrofuran, and cooled at 0° C. in ice-bath, was combined with 0.67 ml (0.0048 mole) of triethylamine and then with 0.5 ml (0.0048 mole) of isobutyroyl chloride dissolved in 5 ml of tetrahydrofuran. The resulting suspension was stirred for 1½ hours, brought to room temperature and evaporated to dryness under vacuum. The crude product obtained was taken up with chloroform and washed with water. The separated organic layer was dried over sodium sulphate and evaporated to dryness. 1.4 g of 3-(2'-chloroethyl)-2,3-dihydro-7-isobutyroyloxy- 4H-1,3-benzoxazin-4-one were obtained and used as such in the next step.

B) From 1.4 g (0.004 mole) of the compound obtained under A), and following the procedure used in Example 1D, 0.9 g of the title compound were obtained. m.p. 70°–71° C. (methylene chloride).

$^1$H-NMR 7.85 (d, 1H); 6.95 (m, 2H); 5.41 (s, 2H); 4.72 (t, 2H); 3.86 (t, 2H); 2.48 (m, 1H); 1.25 (d, 6H)

$^{13}$C-NMR 174.75; 161.51; 158.77; 155.15; 129.78; 116.40; 110.34; 78.71; 71.71; 41.42; 33.60; 18.79 (2C)

EXAMPLE 8

2,3-Dihydro-7-isobutyloxycarbonyloxy-3-(2'-nitrooxy-ethyl)-4H-1,3-benzoxazin-4-one A) A solution of 1 g (0.0044 mole) of the compound obtained in Example 6B, in 10 ml of tetrahydrofuran, and cooled at 0° C. in ice-bath, was combined with 0.67 ml (0.0048 mole) of triethylamine and then with 0.63 ml (0.0048 mole) of isobutylchloroformate dissolved in 5 ml of tetrahydrofuran. The resulting suspension was stirred for 1 hour at 0° C., then heated to room temperature and evaporated to dryness under vacuum. The crude obtained was taken up with chloroform and washed with water. The separated organic layer was dried over sodium sulphate and evaporated to dryness. 1.4 g of 3-(2'-chloro-ethyl)-2,3-dihydro-7-isobutyloxycarbonyloxy-4H-1,3-benzoxazin-4-one were obtained and used as such in the next step.

B) From 1.2 g (0.003 mole) of the compound obtained under A), and following the procedure used in Example 1D, 1.2 g of the title compound were obtained. m.p. 82°–84° C. (methylene chloride).

$^1$H-NMR 7.86 (d, 1H); 7.08 (s, 1H); 7.06 (d, 1H); 5.42 (s, 2H); 4.72 (t, 2H); 4.04 (d, 2H); 3.86 (t, 2H); 2.00 (m, 1H); 0.96 (d, 6H)

$^{13}$C-NMR 161.41; 158.76; 155.00; 152.59; 129.47; 116.66; 116.21; 109.93; 78.74; 74.76; 71.70; 41.35; 27.43; 18.90 (2C)

EXAMPLE 9

2,3-Dihydro-7-(N-ethylcarbamoyloxy)-3-(2'-nitrooxy-ethyl)-4H-1,3-benzoxazin-4-one A) A solution of 1 g (0. 0044 mole) of the compound obtained in Example 6B, in 10 ml of tetrahydrofuran, and cooled at 0° C., was combined with 0.06 ml (0.0004 mole) of triethylamine and then with 0.42 ml (0.0052 mole) of ethyl isocyanate dissolved in 5 ml of tetrahydrofuran. The resulting suspension was stirred for 1 hour at room temperature. 0.1 ml (0.001 mole) of ethylchloroformate was added in portions and, after 7 hours, the reaction mixture was evaporated to dryness under vacuum. The crude product obtained was taken up with chloroform and washed with water. 1.2 g of 3-(2'-chloroethyl)-2,3-dihydro-7-(N-ethylcarbamoyloxy)- 4H-1,3-benzoxazin-4-one were obtained and used as such in the next step.

B) From 1 g (0.003 mole) of the compound obtained under A), and following the procedure used in Example 1D, 0.9 g of the title compound were obtained. m.p. 113°–115° C. (ethyl acetate/n-hexane 1:1).

$^1$H-NMR 7.92 (t, 1H); 7.80 (d, 1H); 6.92 (dd, 1H); 6.88 (d, 1H); 5.39 (s, 2H); 4.72 (t, 2H); 3.85 (t, 2H); 3.11 (m, 2H); 1.10 (t, 3H)

$^{13}$C-NMR 161.64; 158.72; 155.84; 153.44; 129.13; 116.48; 115.45; 109.73; 78.67; 71.73; 41.37; 35.64; 15.03

EXAMPLE 10

2,3-Dihydro-6-(N-isobutyloxycarbonyl)-3-(2'-nitrooxyethyl)- 4H-1,3-benzoxazin-4-one A) A solution of 3.9 ml (0.053 mole) of thionyl chloride in 50 ml of chloroform was added to a solution of 5.35 g (0.025 mole) of the compound obtained in Example 2A, in 100 ml of chloroform, at 0° C. At the end of the addition the solution was heated to reflux for 8 hours. The mixture was then brought to room temperature, and evaporated under vacuum. 5.5 g of 6-amine-3-(2'-chloroethyl)- 2,3-dihydro-4H-1,3-benzoxazin-4-one were obtained and used as such in the next step.

B) A solution of 2 g (0.007 mole) of the compound obtained under A), in 20 ml of methylene chloride, and cooled at 0° C., was combined with a solution of 0.64 g of sodium bicarbonate in 10 ml of water. 8.32 ml (66.88 mole) of isobutylchloroformate dissolved in 80 ml of methylene chloride and 5.6 g (66.88 mole) of sodium hydrocarbonate dissolved in 80 ml of water were a simultaneously added dropwise over 6 hours to the reaction mixture at 0° C. The resulting mixture was washed with water, and the separated organic layer was dried over sodium sulphate and evaporated under vacuum. 2.2 g of the crude product obtained were purified by flash chromatography on silica gel, eluting with methylene chloride/acetone 9:0.5, to give 1.6 g of 3-(2'-chloroethyl)-6-isobutyloxycarbonylamine-2,3-dihydro-4H-1,3-benzoxazin-4-one used as such in the next step.

C) From 1.4 g (0.004 mole) of the compound obtained under B), and following the procedure used in Example 1D, 1.1 g of the title compound were obtained. m.p. 130° C. (methylene chloride).

$^1$H-NMR 9.71 (s, 1H); 7.96 (d, 1H); 7.58 (dd, 1H); 7.03 (d, 1H); 5.32 (s, 2H); 4.71 (t, 2H); 3.89 (d, 2H); 3.85 (m, 2H); 1.94 (m, 1H); 0.95 (d, 6H)

13C-NMR 161.90; 154.02; 153.10; 135.40; 124.81; 118.68; 117.01 (2C); 78.41; 71.73; 70.43; 41.49; 27.84; 19.18 (2C)

EXAMPLE 11

2,3-Dihydro-6-(N'-ethyl-ureido)-3-(2'-nitrooxyethyl)-4H-1,3-benzoxazin-4-one

A) A solution of 0.601 g (0.007 mole) of ethyl isocyanate, in 10 ml of methylene chloride, and cooled at 0° C., was combined with 2 g (0.007 mole) of the compound obtained in Example 10A dissolved in 20 ml of methylene chloride and 1.05 ml (0.007 mole) of triethylamine. The resulting solution was stirred at 0° C., and 12 ml (152 moles) of ethyl isocyanate were added over 18 hours. The solution was heated to room temperature, washed with 100 ml of HCl 1N, water and a solution of 5% sodium bicarbonate to neutral pH. The separated organic layer was dried over sodium sulphate and evaporated under vacuum. 1.8 g of 3-(2'-chloroethyl)-6-(N'-ethyl-ureido)-2,3-dihydro-4H-1,3-benzoxazin- 4-one were obtained and used as such in the next step.

C) From 1 g (0.003 mole) of the compound obtained under A), and following the procedure used in Example 1D, 0.6 g of the title compound were obtained. m.p. 142°–144° C. (methylene chloride).

$^1$H-NMR 8.51 (s, 1H); 7.86 (d, 1H); 7.51 (dd, 1H); 6.96 (d, 1H); 6.08 (t, 1H); 5.30 (s, 2H); 4.71 (t, 2H); 3.84 (t, 2H); 3.11 (m, 2H); 1.06 (t, 3H)

$^{13}$C-NMR 162.06; 155.41; 152.18; 135.87; 124.45; 118.58; 116.73; 116.45; 78.37; 71.75; 41.45; 34.28; 15.74

The following compounds of formula I were prepared according to the methods of the foregoing examples starting from the appropriate precursors:

7-acetamido-2,3-dihydro-3-(2'-nitrooxyethyl)-4H-1,3-benzoxazin- 4-one 7-acetyloxy-2,3-dihydro-3-(2'-nitrooxyethyl)-4H-1,3-benzoxazin- 4-one 2,3-dihydro-6-dimethylamine-3-(2'-nitrooxyethyl)-4H-1,3-benzoxazin-4-one 2,3-dihydro-7-guanidino-3-(2'-nitrooxyethyl)-4H-1,3-benzoxazin- 4-one 6-carboxyethyl-2,3-dihydro-3-(2'-nitrooxyethyl)-4H-1,3-benzoxazin-4-one 7-carboxamido-2,3-dihydro-3-(2'-nitrooxyethyl)-4H-1,3-benzoxazin- 4-one 2,3-dihydro-6-nitro-3-(5'-nitrooxypentyl)-4H-1,3-benzoxazin- 4-one 6-cyano-2,3-dihydro-3-(2'-nitrooxyethyl)-4H-1,3-benzothiazin- 4-one 6-carboxy-2,3-dihydro-3-(2'-nitrooxyethyl)-4H-1,3-benzoxazin- 4-one 2,3-dihydro-6-(N,N-dimethylcarbamoyl)-3-(2'-nitrooxyethyl)- 4H-1,3-benzoxazin-4-one 2,3-dihydro-6-guanidino-3-(2'-nitrooxyethyl)-4H-1,3-benzoxazin- 4-one 2,3-dihydro-6-(N$^G$-methylguanidino)-3-(2'-nitrooxyethyl)-4H-1,3-benzoxazin-4-one 2,3-dihydro-6-(N-ethylcarbamoyloxy)-3-(2'-nitrooxyethyl)-4H-1,3-benzoxazin-4-one 2,3-dihydro-6-isobutyloxycarbonyloxy-3-(2'-nitrooxyethyl)- 4H-1,3-benzoxazin-4-one 2,3-dihydro-7-dimethylamine-3-(2'-nitrooxyethyl)-4H-1,3-benzoxazin-4-one 2,3-dihydro-6-isobutyloxycarbonyloxy-3-(2'-nitrooxyethyl)- 4H-1,3-benzoxazin-4-one 2,3-dihydro-7-(N'-ethyl-ureido)-3-(2'-nitrooxy-ethyl)-4H-1,3-benzoxazin-4-one 2,3-dihydro-7-(N'N'-dimethyl-N-formimido)-3-(2'-nitrooxyethyl)- 4H-1,3-benzoxazin-4-one 2,3-dihydro-7-nitro-3-(2'-nitrooxyethyl)-4H-1,3-benzoxazin- 4-one 2,3-dihydro-7-cyano-3-(2'-nitrooxyethyl)-4H-1,3-benzoxazin- 4-one.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A compound of formula I

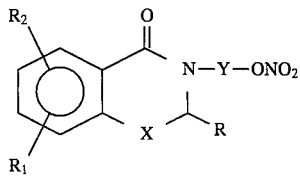

wherein

R represents hydrogen, $C_1$–$C_6$ alkyl, $C_5$–$C_7$ cycloalkyl, methylene-dioxy or phenyl which may be substituted by one or two groups independently selected from hydroxy, halogen, nitro, $C_1$–$C_6$ alkyl or $C_1$–$C_6$ alkoxy; $R_1$ and $R_2$ independently represent hydrogen, —COOR$_3$ , —CONR$_4$R$_5$,

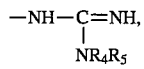

—OCONR$_4$R$_5$, —OCOR$_3$, —OCOOR$_6$, —NR$_3$CONR$_4$R$_5$, —N=CH—NR$_4$R$_5$, CN, OH or H, wherein R$_3$ is hydrogen or $C_1$–$C_6$ alkyl, and R$_4$ and R$_5$ independently are hydrogen or $C_1$–$C_6$ alkyl, R$_6$ is $C_1$–$C_6$ alkyl, with the proviso that R$_1$ and R$_2$ cannot be hydrogen at the same time; X is oxygen or sulphur; Y represents an ethylene group; or a pharmaceutically acceptable salt thereof.

2. A compound according to claim 1, wherein said compound is selected from the group consisting of benzoxazin- 4-one; 7-acetyloxy-2,3-dihydro-3-(2'-nitrooxyethyl)-4H-1, 3-benzoxazin-4-one; 2,3-dihydro-6-dimethylamine- 3-(2'-nitrooxyethyl)-4H-1,3-benzoxazin-4-one; 2,3-dihydro-7-guanidino-3-(2'-nitrooxyethyl)-4H-1,3-benzoxazin- 4-one; 6-carboxyethyl-2,3-dihydro-3-(2'-nitrooxyethyl)- 4H-1,3-benzoxazin-4-one; 7-carboxamido-2,3-dihydro-3-(2'-nitrooxyethyl)-4H-1,3-benzoxazin-4-one; 2,3-dihydro- 6-nitro-3-(5'-nitrooxypentyl)-4H-1,3-benzoxazin-4one; 6-cyano-2,3-dihydro-3-(2'-nitrooxyethyl)-4H-1,3-benzothiazin-4-one; 6-carboxy-2,3-dihydro-3-(2'-nitrooxyethyl)- 4H-1,3-benzoxazin-4-one; 2,3-dihydro-6-(N,N-dimethylcarbamoyl)-3-(2'-nitro-oxyethyl)-4H-1,3-benzoxazin-4-one; 2,3-dihydro-6-guanidino-3-(2'-nitrooxyethyl)-4H-1,3-benzoxazin- 4-one; 2,3-dihydro-6-(N-methylguanidino)-3-(2-nitrooxy-ethyl)-4H-1,3-benzoxazin-4-one; 2,3-dihydro-6-(N-ethylcarbamoyloxy)- 3-(2'-nitrooxy-ethyl)-4H-1,3-benzoxazin-4-one; 2,3-dihydro-6-isobutyloxycarbonyloxy-3-(2'-nitrooxy-ethyl)- 4H-1,3-benzoxazin-4-one; 2,3-dihydro-7-dimethylamine- 3-(2'-nitrooxyethyl)-4H-1,3-benzoxazin-4-one; 2,3-dihydro-6-isobutyloxycarbonyloxy-3-(2'-nitrooxy-ethyl)-4H-1,3-benzoxazin-4-one; 2,3-dihydro-7-(N'-ethyl-ureido)-3(2'-nitrooxy-ethyl)-4H-1,3-benzoxazin-4-one; 2,3-dihydro-7-(N',N'-dimethyl-N-formimido)- 3-(2'-nitrooxyethyl)-4H-1,3-benzoxazin-4-one; 2,3-dihydro-7-nitro-3-(2'-nitrooxyethyl)4H-1,3-benzoxazin-4-one; and 2,3-Dihydro-7-cyano-3-(2'-nitrooxyethyl)- 4H-1,3-benzoxazin-4-one; 2,3-dihydro-3-(2'-nitrooxyethyl)- 6-nitro-4H-1,3-benzoxazin-4-one; 6-acetamido-2,3-dihydro-3-(2'-nitrooxyethyl)-4H- 1,3-benzoxazin-4-one; 2,3-dihydro-6-(N'N'-dimethyl-N-formimido)-3-(2'-nitro-oxyethyl)-4H-1,3-benzoxazin-4-one; 2,3-dihydro-6-hydroxy-3-(2'-nitrooxyethyl)-4H-1,3-benzoxazin-4-one; 2,3-dihydro-7-hydroxy-3-(2'-nitrooxyethyl)-4H-1,3-benzoxazin-4-one; 2,3-dihydro-7-isobutyroyloxy-3-(2'-nitrooxyethyl)-4H-1,3-benzoxazin-4-one; 2,3-dihydro-7-isobutyloxycarbonyloxy-3-(2'-nitrooxy-ethyl)-4H- 1,3-benzoxazin-4-one; 2,3-dihydro-7-(N-ethylcarbamoyloxy)-3(2'-nitrooxy-ethyl)-4H-1,3-benzoxazin-4-one; 2,3-dihydro- 6-(N-isobutyloxycarbonyl)-3-(2'-nitrooxy- ethyl)-4H-1,3-benzoxazin-4-one; 2,3-dihydro-6-(N'-ethyl-ureido)-3-( 2'-nitrooxyethyl)-4H-1,3-benzoxazin-4-one and the pharmaceutically acceptable salts thereof.

3. A pharmaceutical composition for use in the treatment of cardiovascular disease, comprising a therapeutically effective amount of a compound as defined in claim 1, and a pharmaceutically acceptable carrier.

4. The pharmaceutical composition of claim 3, wherein the composition is in a form selected from the group consisting of uncoated tablets, coated tablets, syrups and vials.

5. The pharmaceutical composition of claim 4, wherein said coated tablet is coated with sugar, a biologically acceptable film or both.

6. A method for treating cardiovascular disease, comprising administering to a subject in need thereof, a therapeutically effective amount of a compound of formula I

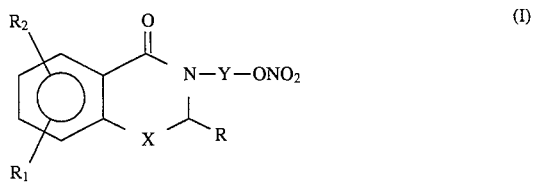

wherein

R represents hydrogen, $C_1$–$C_6$ alkyl, $C_5$–$C_7$ cycloalkyl, methylene-dioxy or phenyl which may be substituted by one or two groups independently selected from hydroxy, halogen, nitro, $C_1$–$C_6$ alkyl or $C_1$–$C_6$ alkoxy; $R_1$ and $R_2$ independently represent hydrogen, —COOR$_3$, —CONR$_4$R$_5$,

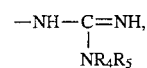

—OCONR$_4$R$_5$, —OCOR$_3$, —OCOOR$_6$, —NR$_3$CONR$_4$R$_5$, —N═CH—NR$_4$R$_5$, CN, OH, SR$_3$, wherein $R_3$ is hydrogen or $C_1$–$C_6$ alkyl, and $R_4$ and $R_5$ independently are hydrogen or $C_1$–$C_6$ alkyl, $R_6$ is $C_1$–$C_6$ alkyl, with the proviso that $R_1$ and $R_2$ cannot be hydrogen at the same time; X is oxygen or sulphur; Y represents an ethylene group; or a pharmaceutically acceptable salt thereof.

7. The method of claim 6, wherein said compound of formula I is administered as a pharmaceutical composition comprising an effective amount of said compound of formula I and a carrier.

8. The method of claim 6, wherein said compound of formula I is administered to said subject orally, intramuscularly or intravenously.

9. A compound selected from the group consisting of: 7-acetamido-2,3-dihydro-3-(2'nitrooxyethyl)-4H-1,3-benzoxazin-4one; 6-acetamido-2,3-dihydro-3-(2'nitrooxyethyl)-4H-l, 3-benzoxazin- 4-one; and the pharmaceutically acceptable salts thereof.

* * * * *